(12) United States Patent
Shirasawa et al.

(10) Patent No.: US 7,795,475 B2
(45) Date of Patent: Sep. 14, 2010

(54) REACTION DEVICE

(75) Inventors: Takeshi Shirasawa, Wakayama (JP); Yasukazu Kumita, Wakayama (JP); Eiji Saito, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/524,166

(22) PCT Filed: Jan. 31, 2008

(86) PCT No.: PCT/JP2008/052004

§ 371 (c)(1),
(2), (4) Date: Jul. 23, 2009

(87) PCT Pub. No.: WO2008/093898

PCT Pub. Date: Aug. 7, 2008

(65) Prior Publication Data

US 2010/0010268 A1  Jan. 14, 2010

(30) Foreign Application Priority Data

Jan. 31, 2007  (JP) .............................. 2007-021000

(51) Int. Cl.
*C07C 45/00* (2006.01)
*B01J 19/00* (2006.01)

(52) U.S. Cl. .................. 568/426; 568/485; 422/222
(58) Field of Classification Search ................. 568/420, 568/426, 485; 422/222
See application file for complete search history.

(56) References Cited

U.S. PATENT DOCUMENTS

2005/0272958 A1 *  12/2005  Hasegawa et al. ........... 568/471

FOREIGN PATENT DOCUMENTS

| DE | 25 17 859 | 3/1976 |
|---|---|---|
| EP | 0 263 385 | 4/1988 |
| EP | 0 529 804 | 3/1993 |
| EP | 1 604 739 | 12/2005 |
| GB | 2 068 938 | 8/1981 |
| JP | 2004 10568 | 1/2004 |
| JP | 2004 501881 | 1/2004 |

* cited by examiner

*Primary Examiner*—Sikarl A Witherspoon
(74) *Attorney, Agent, or Firm*—Oblon, Spivak, McClelland, Maier & Neustadt, L.L.P.

(57) ABSTRACT

A reaction device according to the present invention is used in production of aldehyde from alcohol. The reaction device includes a reactor having a reaction field where a catalyst is provided inside and a reaction fluid flows. The catalyst has a surface extending in the direction of flow of the reaction fluid and contains Cu.

18 Claims, 4 Drawing Sheets

FIG. 4

REACTION DEVICE

TECHNICAL FIELD

The present invention relates to a reaction device used for producing aldehyde from alcohol and an aldehyde production method using the reaction device

BACKGROUND ART

Aldehyde is a useful compound as a material used in a chemical reaction or a perfume material and is conventionally composed by a dehydrogenation reaction, an oxidation reaction or the like using alcohol as a raw material. Among those reactions, a dehydrogenation reaction is an endothermic reaction, whereas an oxidation reaction which is an exothermic reaction, and thermal control during the dehydrogenation reaction can be easily achieved. Therefore, a dehydrogenation reaction has been used for an aldehyde production method in many cases. An aldehyde production method using a dehydrogenation reaction include, for example, a method in which a suspension is reacted using a catalyst in a batch manner, a method in which a suspension is reacted continuously using a catalyst, a method in which a reaction solution is continuously supplied to a reaction field (fixed bed) in which a catalyst formed into a predetermined shape is filled, thereby leading to a reaction, and like method.

In a dehydrogenation reaction, ester which is a dimerized aldehyde as a by-product is generated as well as aldehyde which is aimed to obtain. To cope with this, various improvements have been made to techniques for suppressing the generation of such a by-product and thus highly selectively causing a reaction. For example, in Patent Reference 1, a production method in which a dehydrogenation reaction is performed in a liquid phase using a ruthenium complex catalyst to store generated aldehyde in a gas state is disclosed. Also, Patent Reference 2 discloses a method in which alcohol is dehydrogenated by a low pressure gas phase reaction at a fixed bed to highly selectively generate aldehyde.

Patent Reference 1: Japanese Laid-Open Publication No. 2004-10568

Patent Reference 2: Japanese Translation of PCT International Application No. 2004-501881

DISCLOSURE OF THE INVENTION

A reaction device according to the present invention is used in production of aldehyde from alcohol.

The reaction device of the present invention includes a reactor having a reaction field where a catalyst is provided inside and a reaction fluid flows.

The catalyst has a surface extending in a direction of flow of the reaction fluid and contains Cu.

An aldehyde production method according to the present invention is a method in which aldehyde is produced from alcohol.

According to the aldehyde production method of the present invention, a reaction fluid containing alcohol is made to flow and react in a reaction field where a catalyst having a surface extending in a direction of flow of the reaction fluid and contains Cu is provided, thereby producing aldehyde.

DETAILED DESCRIPTION OF THE INVENTION

Hereafter, embodiments will be described with the accompanying drawings.

Embodiment 1

<Reaction Device>

Figure 1:
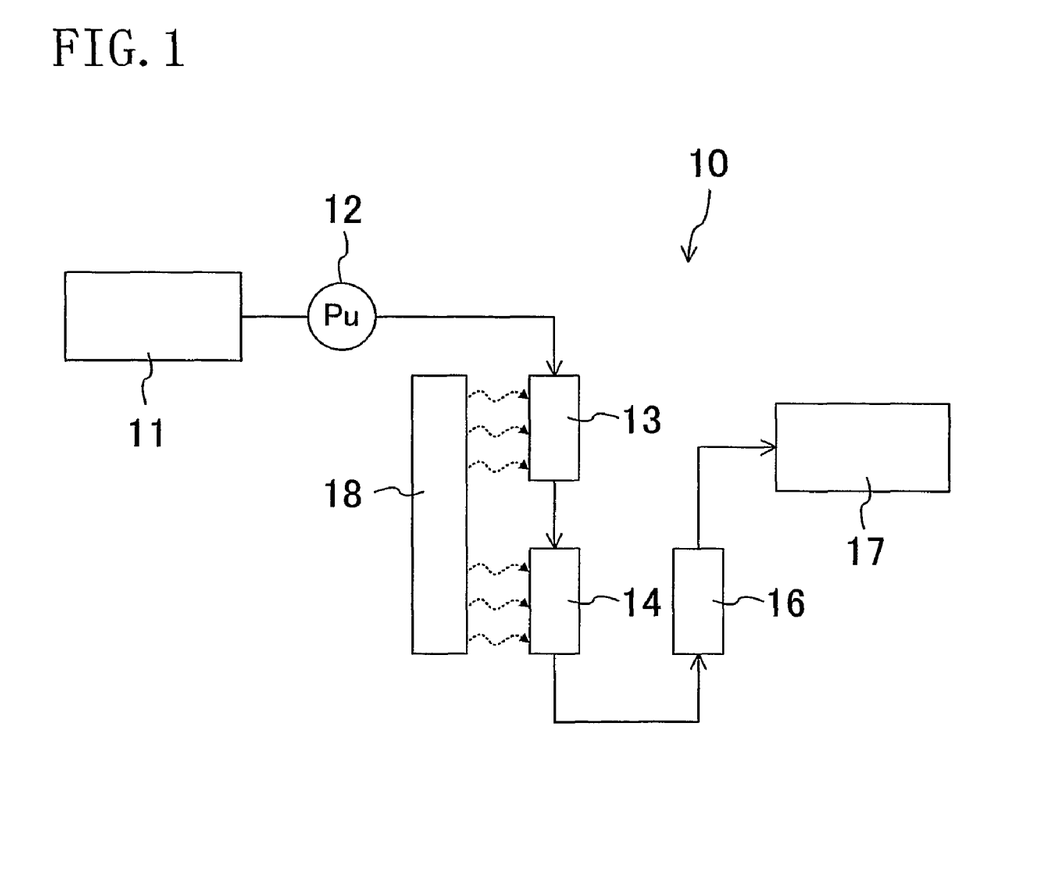
FIG. 1 is a diagram illustrating a structure of a reaction device according to Embodiment 1.

FIG. 1 shows a reaction device 10 according to Embodiment 1.

The reaction device 10 is a continuous type and is capable of continuously producing a reaction product. The reaction device 10 includes a pipe extending from a raw material alcohol supplier 11, which is a raw material alcohol source, to a product reservoir 17. The reaction device 10 also includes a raw material supplying pump 12, a preheating section 13, a reactor 14 and a cooler 16 which are provided in series at some midpoints in the pipe in this order from the upper reach to the lower reach with intervals therebetween. The reaction device 10 further includes a heater 18 which is provided so as to heat the preheating section 13 and the reactor 14. Note that a pressure regulator (not shown) is provided upstream of the product reservoir 17.

The reaction device 10 is used for production of aldehyde in the following manner. A reaction fluid, i.e., a mixture of alcohol as a reaction material, is supplied from the raw material alcohol supplier 11 to the preheating section 13 via the raw material supplying pump 12. Next, the reaction fluid is preheated in the preheating section 13, the preheated reaction fluid is supplied from the preheating section 13 to the reactor 14, and alcohol is reacted in the reactor 14 so that aldehyde and hydrogen are produced. The reaction fluid containing the produced aldehyde is supplied from the reactor 14 to the cooler 16, cooled and condensed. Then, the reaction fluid obtained from the cooler 16 is stored in the product reservoir 17.

The reactor 14 has an inlet through which the reaction fluid enters and an outlet through which the reaction fluid exits. The reactor 14 also has inside a reaction path 14a formed in the form of an elongated hole so as to be located between the inlet and the outlet. The reaction path 14a constitutes a reaction field 15 in which the reaction fluid flows through and reacts.

In the reactor 14, the reaction path 14a may be formed such that a flat member which has a groove formed in its surface by cutting or any other processing is tightly joined with another flat member. Alternatively, the reaction path 14a may be formed by a tubular member already complete, such as a square tube, a circular tube, or the like.

The cross-sectional shape of the reaction path 14a may be, for example, circular, semicircular, elliptic, semielliptic, square, rectangular, trapezoidal, parallelogramic, indeterminate or the like. The longitudinal passage of the reaction path 14a between the inlet and the outlet may have a linear shape, a circular shape, a meander shape, a spiral shape or the like.

The reaction path 14a which constitutes the reaction field 15 is provided with a catalyst 19. The catalyst 19 has a surface extending in the direction of flow of the reaction fluid.

Preferable examples of the catalyst 19 include Cu and metal composites containing Cu. As metals capable of binding to Cu, any of the metals of Group 6 to Group 12, such as Ni, Pd, Pt and the like, can be preferably used. As metal composites containing Cu, for example, two component metals obtained by adding a transition metal element such as Cr, Co, Ni, Fe, Mn and the like to Cu can be used. The catalyst 19 may be any of these being supported by silica, alumina, titania, zeolite or the like, or having a controlled oxidation state. Of these materials, the catalyst 19 is preferably Cu or an alloy containing Cu, in view of ease of processing, reactivity and economic efficiency, and is more preferably composed of a simple substance of Cu. The catalyst 19 composed of a simple substance of Cu preferably contains highly pure Cu, and a material having a purity of 99.0% or more is preferable. Note that Cu might be rust-proofed in the course of marketing, but Cu which has not been rust-proofed is preferable.

Figure 3:
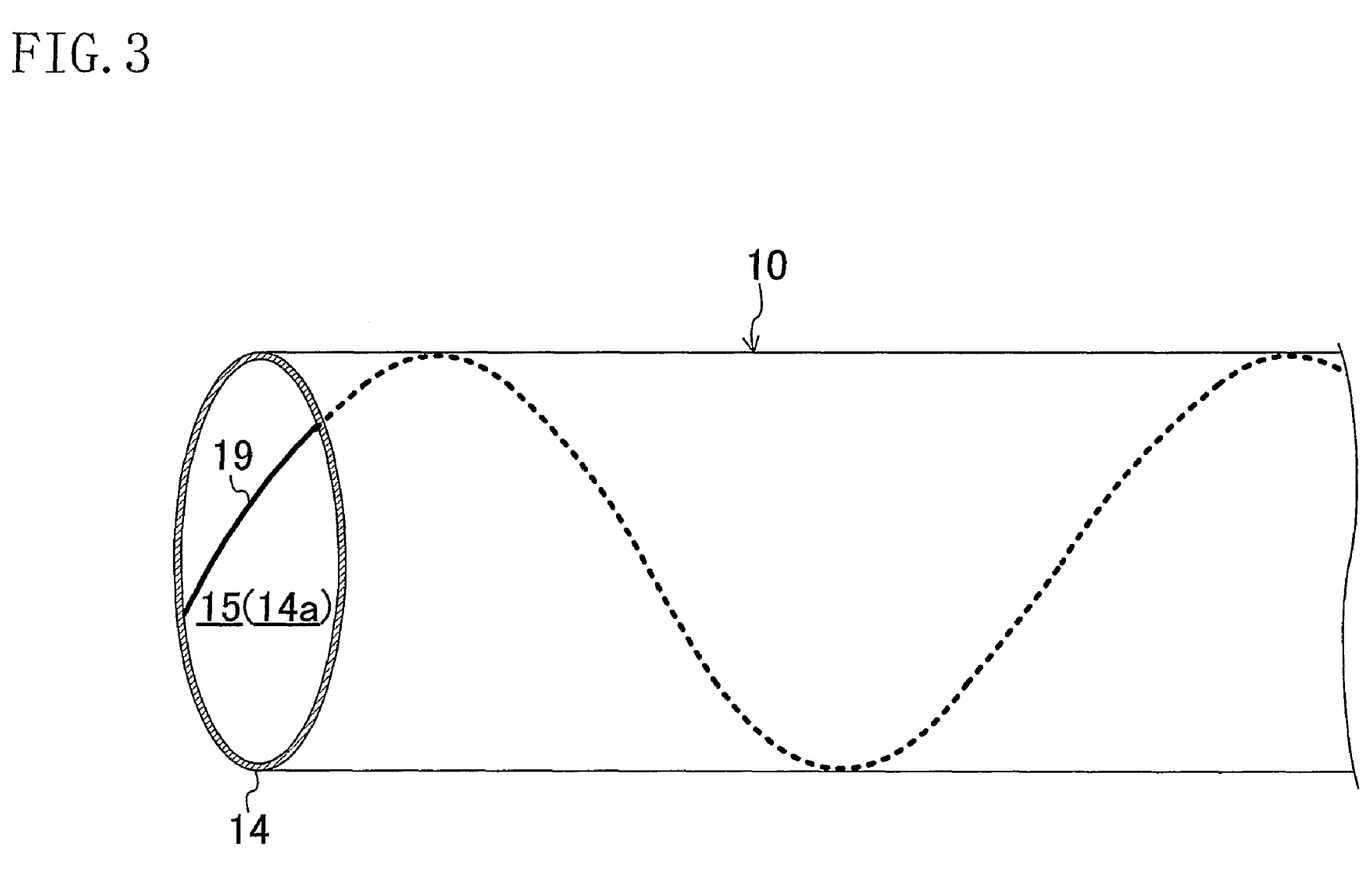
FIG. 3 is a perspective view of a reactor.

As shown in FIG. 2(*a*) and FIG. 2(*b*), the catalyst 19 is in the form of, for example, an elongated structure, e.g., a linear structure such as a metal wire, a bundle of wires, or a stranded cable, or an elongated plate structure. Alternatively, as shown in FIG. 2(*c*) or FIG. 2(*d*), the catalyst 19 constitutes the inner wall of the reaction path 14*a* inside the reactor 14. The catalyst 19 may have a shape continuously extending in the direction of flow of the reaction fluid. Alternatively, the catalyst 19 may include a plurality of separate parts aligned with intervals in the direction of flow of the reaction fluid.

Where the catalyst 19 is in the form of an elongated structure, the outer surface corresponds to a surface extending in the direction of flow of the reaction fluid. In this case, the reactor 14 having the reaction path 14*a* formed by flat members may have the catalyst 19 in the groove formed in one of the flat members. The reactor 14 having the reaction path 14*a* formed by a tubular member already complete may have the catalyst 19 inserted in the reaction path 14*a*. Alternatively, the catalyst 19 may be provided in the reaction path 14*a* in the form of a spiral at a certain pitch in the direction of flow of the reaction fluid as shown in FIG. 3. Still alternatively, a plurality of parts of the catalyst 19 may be aligned with intervals in the direction of flow of the reaction fluid such that the parts as a whole constitute a surface extending in the direction of flow of the reaction fluid. The catalyst 19 may be provided entirely across the whole reach of the reactor 14 between the inlet and the outlet or may be provided partially over the reach of the reactor 14 between the inlet and the outlet.

Where the inner wall of the reaction path 14*a* is formed by the catalyst 19, the surface of the inner wall corresponds to the surface extending in the direction of flow of the reaction fluid. In this case, a material used for the inner wall of the reaction path 14*a* may be a catalyst material. Alternatively, the inner wall of the reaction path 14*a* may be coated with the catalyst 19 by plating, sputtering, painting and drying, or any other technique after general construction of the reaction path 14*a*. The inner wall may be partially formed by a catalyst material such that parts of the wall are located with intervals in the direction of flow of the reaction fluid. The catalyst 19 may be provided entirely across the whole reach of the reactor 14 between the inlet and the outlet or may be provided partially over the reach of the reactor 14 between the inlet and the outlet.

An applicable index indicative that the catalyst 19 has a surface extending in the direction of flow of the reaction fluid is "A2/A1" where A1 is the surface area of a unit of catalyst and A2 is the projected area of the unit of catalyst on a plane perpendicular to the direction of flow of the reaction fluid. The "unit of catalyst" refers to one of particles of catalyst, one of lines of catalyst, or one of a series of foils of catalyst. Specifically, in the case where the catalyst is in the form of spherical particles, A2/A1=0.25(−). In the case where the catalyst has a cylindrical shape with a diameter D and a length L, the value of A2/A1 varies depending on the installment direction of the catalyst. For example, in the case where the catalyst is installed such that the direction of the length of the catalyst, L, is identical to the direction of flow of the reaction fluid and L=2D, A2/A1=0.1(−). In the case where the catalyst exists in the inner wall of the reaction path 14*a* and the reaction fluid passes through the reaction path 14*a* to react, the projected area A2 is 0 (A2=0), and hence, A2/A1=0(−).

In a reaction device having a plurality of units of catalyst, $\Sigma A2/\Sigma A1$ (where $\Sigma A1$ is the total sum of surface areas A1 of catalyst units and $\Sigma A2$ is the total sum of projected areas A2 of the catalyst units) can be used as the aforementioned index. Note that, in this specification, the total sums are represented by $\Sigma A1$ and $\Sigma A2$ even in a case where the reaction device only has one catalyst unit.

The value of $\Sigma A2/\Sigma A1$ is preferably 0 to 0.1(−), more preferably 0 to 0.07(−), and even more preferably 0 to 0.05 (−).

Figure 2A:
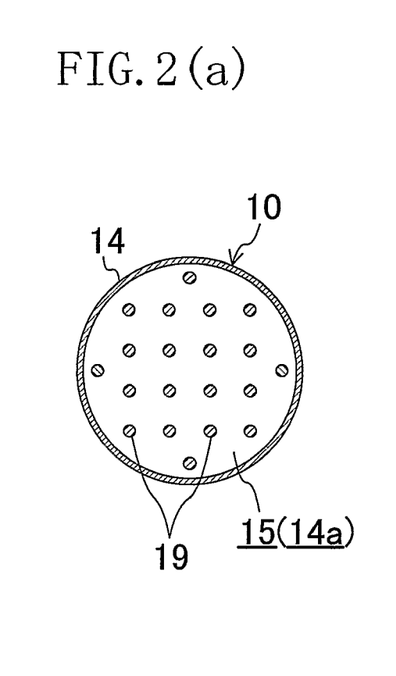
FIGS. 2(a) through 2(d) are cross-sectional views of a reactor.
Figure 2B:
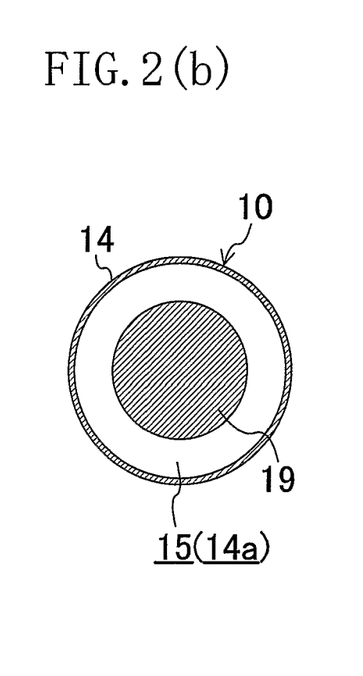
Figure 2C:
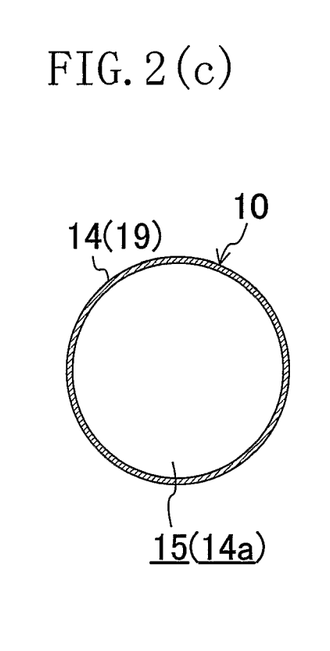
Figure 2D:
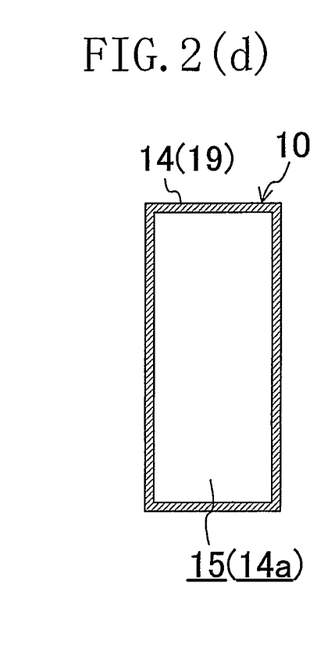

The catalyst 19 is preferably provided in the reaction path 14*a* such that, in any traverse section of the reaction path 14*a*, the catalyst 19 exists in the area of radius of 10 mm. More preferably, the catalyst 19 exists in the area of radius of 5 mm. With such an arrangement, the distance between the reaction fluid and the catalyst 19 is 20 mm or less at any location in the reaction field 15, so that desirable reactivity and aldehyde selectivity are achieved. Specifically, for example, as shown in FIG. 2(*d*), the reaction path 14*a* may be in the form of an elongated slit in which the inner wall is formed by the catalyst 19 and a traverse section has a space of 20 mm or less.

In the case where the reaction path 14*a* is formed by a plurality of catalyst units of the catalyst 19, the reaction path 14*a* is preferably structured such that the reaction fluid flows smoothly in the vicinity of the catalyst 19 without stagnation. If without a stagnation region (i.e., dead space) in the vicinity of the catalyst 19, the reaction residence time distribution of the reaction fluid can be narrowed, whereby the reaction fluid residing in the reaction path 14*a* for a long time is prevented from causing a side reaction, such as carbonization, or the like. Specifically, the catalyst 19 is preferably located such that the catalyst units do not have a point contact with each other or do not have narrow gaps between each other. More specifically, the minimum distance between catalyst units is preferably 0.2 mm or more, more preferably 0.5 mm or more, even more preferably 1 mm or more. Note that a reactor called "microreactor" has a narrow flow path of less than 1 mm, and in such a case, the minimum distance between catalyst units is not limited to the ranges mentioned above so long as no stagnation occurs in the flow path. The catalyst 19 of each of the catalyst units preferably has a smooth flat surface.

The raw material supplying pump 12 supplies the reaction fluid output from the raw material alcohol supplier 11 to the preheating section 13. When the reaction fluid is liquid, examples of the raw material supplying pump 12 include a volute pump, diffuser pump, volute diagonal pump, diagonal pump, axial flow pump, gear pump, screw pump, cam pump, vane pump, piston pump, plunger pump, diaphragm pump, vortex flow pump, viscosity pump, airlift pump, jet pump, electromagnetic pump, etc. Among these examples, a pump which generates small pulsating flow is preferable. This is because advantages in reaction are achieved such that passage of the raw material fluid through the flow path without pulsating flow ensures a uniform and stable flow of the fluid and stable mixing phenomenon at any location in the flow path without causing problems in the reaction, and hence, stoichiometric conditions for desirable reactivity and high selectivity are uniformly achieved. The reaction fluid may be supplied to the preheating section 13 by means of pressure difference instead of using the raw material supplying pump 12. In the case where the reaction fluid is a gas, a pressure cylinder with a gas encapsulated inside, a compressor, a blower, and the like can be used.

Examples of the heating system of the heater 18 include a heat exchange method by means of a heated medium, such as hot oil, vapor, etc., a heat transfer method via contact or radiation with a heating element, such as an electric heater, or the like, a method which utilizes a heat pump, etc.

Considering that the reaction occurs at a high temperature, the above-described components of the reaction device 10 need to be made of a material whose melting point is higher than the reaction temperature. Also, considering that the reaction temperature is desirably reached as early as possible, the components are preferably made of a material with excellent heat conductivity. In view of these respects, each of the components of the reaction device 10 is preferably made of a metal material. Examples of the metal material include single-element metals, such as aluminum, titanium, chromium, iron, cobalt, nickel, copper, zinc, zirconium, etc., and alloys multiply containing these single-element metals. Specific examples of the alloys include austenite steels represented by SUS304 and SUS316, martensite steels represented by SUS420, two-phase stainless steels of ferrite and austenite represented by SUS329, Ni alloys represented by Hastelloy C276 and Inconel 600, titanium alloys represented by 6-4 titanium alloy, etc. As a matter of course, each of the components can be made of one of these materials solely or can be made of two or more of these materials together.

<Method for Producing Aldehyde>

Next, a method for producing aldehyde using the reaction device 10 of this embodiment will be described.

The aldehyde production method of this embodiment is for producing a mixture of aldehyde and hydrogen from alcohol based on Formula 1 shown below.

$$C_nH_m\text{—}CH_2OH \rightarrow C_nH_m\text{—}CHO + H_2 \quad \text{[Formula 1]}$$

According to the aldehyde production method of this embodiment, a reaction fluid, i.e., alcohol as a raw material or a mixture containing alcohol as a raw material is supplied from the raw material alcohol supplier 11 to the preheating section 13 via the raw material supplying pump 12.

Examples of alcohol as a raw material contained in the reaction fluid include saturated or non-saturated, linear or branched-chain aliphatic alcohol having a carbon number of 4 to 36, and alcohol which is expressed by Formula 2 (where R1 is a saturated or non-saturated, linear or branched-chain alkyl or alkenyl group having 4 to 36 carbon atoms, preferably 6 to 22 atoms and more preferably 8 to 18 atoms) is preferable.

$$R_1OH \quad \text{[Formula 2]}$$

Specific examples of such alcohol include butyl alcohol, hexyl alcohol, octyl alcohol, decyl alcohol, lauryl alcohol, myristyl alcohol, cetyl alcohol, stearyl alcohol, arakyl alcohol, behenyl alcohol and the like, and also include Ziegler alcohol obtained by a Ziegler method, oxo alcohol obtained by an oxo method, Guerbet alcohol and the like. One of these alcohols may be solely used or a mixed alcohol of two or more of these alcohols may be used.

Note that any material other than alcohol may be mixed in the reaction fluid as necessary so long as the reactivity and yield are not deteriorated. Examples of the material which can be mixed in the reaction fluid include gases (inert gases) inert to the above-described chemical reaction, such as nitrogen, argon, helium, etc. The reaction fluid may contain, in addition to alcohol, any of organic compounds which do not deteriorate essential reactivity, such as hydrocarbon. In this case, the effect of suppressing a side reaction and increasing aldehyde selectivity can be achieved and, for this reason, the reaction fluid is preferably formed so as to contain as a high content of a compound other than alcohol as possible in the range where essential reactivity is not deteriorated. Specifically, the molar fraction of alcohol is preferably 50 mol % or less and more preferably 20 mol % or less.

According to the aldehyde production method of this embodiment, the reaction fluid is preheated in the preheating section 13.

The preheating time of the reaction fluid is preferably 0.1 second to 1 hour, and more preferably 1 second to 10 minutes. The preheating time of the reaction fluid is determined by the residence time of the reaction fluid in the preheating section 13 and therefore can be controlled by selection of the capacity of the preheating section 13. If the capacity of the preheating section 13 is fixed, the preheating time of the reaction fluid is controlled by setting the feeding speed of the reaction fluid from the raw material supplying pump 12.

The preheating temperature of the reaction fluid is preferably 100° C. to 500° C., and more preferably 200° C. to 350° C. The preheating temperature of the reaction fluid is controlled by adjusting the heating temperature of the preheating section 13 by the heater 18.

According to the aldehyde production method of this embodiment, the preheated reaction fluid is supplied to the reactor 14 from the preheating section 13.

Before the reaction fluid is supplied to the reactor 14, the phase state of the reaction fluid may be any of liquid, gas, and supercritical fluid or may be a mixing state of these phases. After the reaction fluid is supplied to the reactor 14, the reaction fluid is preferably in a gas state. The phase state of the reaction fluid is controlled by adjusting the heating temperature of the reactor 14 by the heater 18 and setting the pressure of the reaction fluid by a pressure regulator (not shown) provided upstream of the product reservoir 17.

As a method for supplying a raw material from the preheating section 13 to the reactor 14, either an up flow method or a down flow method may be used. Note that as a raw material can be supplied to the reactor 14 by a single distribution method or a circulation method.

According to the aldehyde production method of this embodiment, in the reactor 14, alcohol is brought into a chemical reaction represented by the above-described Formula 1, thereby producing aldehyde and hydrogen. In this case, the reaction fluid is acted by the catalyst 19 having a surface extending in the direction of flow of the reaction fluid and containing Cu and causes the above-described chemical reaction while it flows from the inlet of the reactor 14 to the outlet thereof.

The reaction time of the reaction fluid is preferably about 0.1 second to 1 hour, and more preferably 1 second to 10 minutes. The reaction time of the reaction fluid is determined by the residence time (reaction residence time) of the reaction fluid in the reactor 14 and is therefore controlled by setting the feeding speed of the reaction fluid from the raw material supplying pump 12 according to the volume of the reaction field 15. To express the concept of reaction time, where an effective volume of a reactor is denoted by V and a normal state volume of a raw material to be introduced into the reactor in a unit time is denoted by F, a space velocity expressed by F/V is sometimes used. When the reaction fluid is a liquid raw material at room temperature, F is replaced with a volume of the liquid and LHSV (liquid hourly space velocity) may be used. In the case of a catalyst reaction, a catalyst unit quantity (mass, volume and surface area) might be used, instead of the reactor volume V.

The reaction temperature of the reaction fluid is preferably 100° C. to 500° C., and more preferably 200° C. to 350° C. The reaction temperature of the reaction fluid is controlled by adjusting the heating temperature of the reactor 14 by the heater 18.

The pressure of the liquid fluid is preferably set as low as possible. Particularly, it is also preferable that the reaction field 15 is substantially under the vacuum condition. Thus, a side reaction can be suppressed and high aldehyde selectivity can be achieved. Specifically, the pressure of the liquid fluid is preferably 1500 kPa or less, and more preferably 300 kPa or less. Note that in the reactor 14, a pressure loss occurs and a pressure is increased by the pressure loss. Therefore, the reaction path 14a preferably has a cross-sectional shape with which the pressure loss is small. The pressure of the reaction fluid is controlled by adjusting the heating temperature of the reactor 14 by the heater 18 and setting the pressure of the reaction fluid by a pressure regulator (not shown) provided upstream of the product reservoir 17.

According to the aldehyde production method of this embodiment, the reaction fluid containing the produced aldehyde from the reactor 14 is supplied to the cooler 16, cooled and condensed. Then, the reaction fluid obtained from the cooler 16 is stored in the product reservoir 17.

The cooling time of the reaction fluid is preferably 0.1 second to 1 hour, and more preferably 1 second to 10 minutes. The cooling time of the reaction fluid is determined by the residence time of the reaction fluid in the cooler 16 and therefore can be controlled by selection of the capacity of the cooler 16. If the capacity of the cooler 16 is fixed, the cooling time of the reaction fluid is controlled by setting the feeding speed of the reaction fluid from the raw material supplying pump 12.

The cooling temperature of the reaction fluid is preferably 0° C. to 200° C., and more preferably 20° C. to 100° C. The cooling temperature of the reaction fluid is controlled by adjusting the cooling temperature of the reaction fluid by the cooler 16.

The stored aldehyde is purified to have the qualities required for the use thereof, for example, as chemical material, perfume material, etc. The purification of aldehyde may be achieved by means of, e.g., distillation, extraction, absorption or the like.

Production of aldehyde by the use of the above-described reaction device 10 enables production of aldehyde from alcohol with high selectivity because the catalyst 19 which has a surface extending in the direction of flow of the reaction fluid is provided in the reaction field 15.

Embodiment 2

<Reaction Device>

Figure 4:
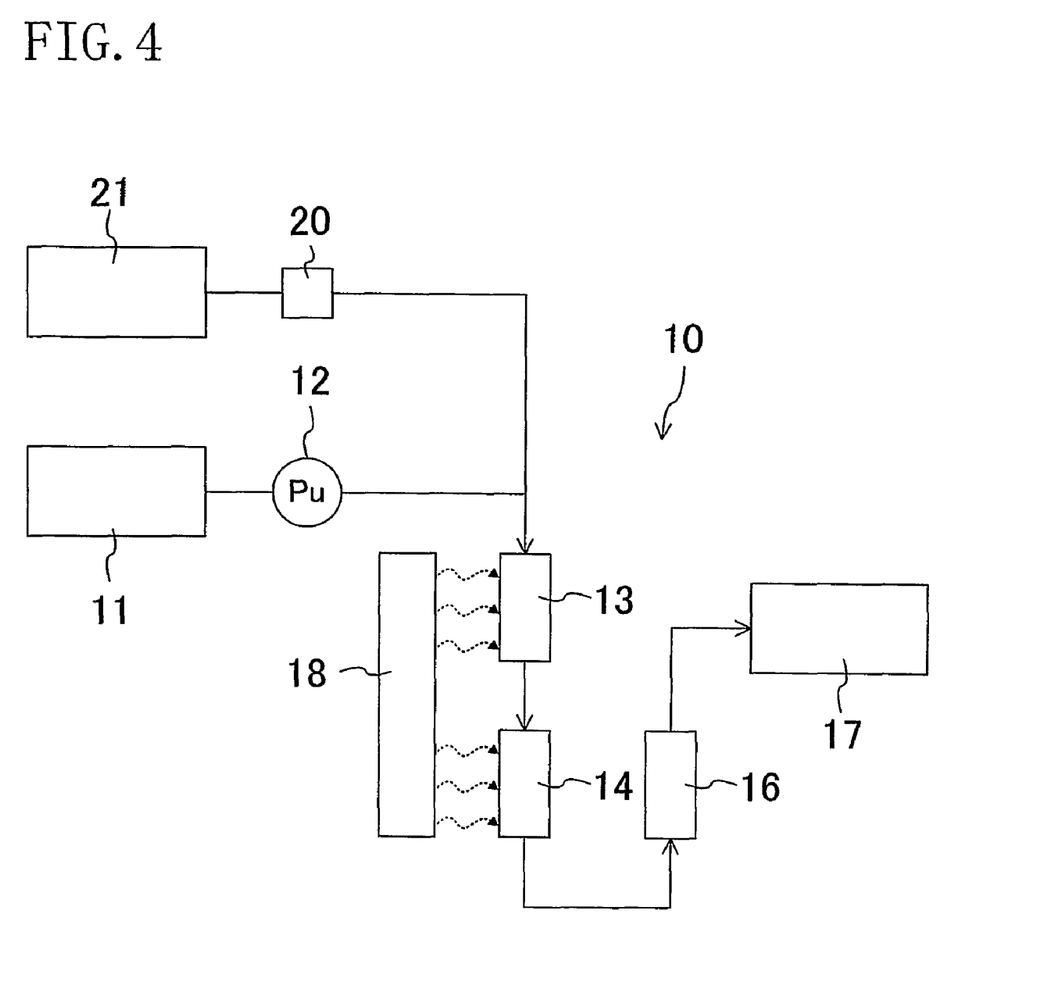
FIG. 4 is a diagram illustrating a structure of a reaction device according to Embodiment 2.

FIG. 4 shows a reaction device 10 according to Embodiment 2. The elements having the same names as those of Embodiment 1 are denoted by the same reference numerals as those of Embodiment 1.

The reaction device 10 includes a pipe which extends from a gas supplier 20 and on which a flow volume controller 21 is provided at a midpoint. The pipe is connected to a point between a raw material supplying pump 12 and a preheating section 13 on a pipe extending from a raw material alcohol supplier 11 to a product reservoir 17.

Other than that, the reaction device 10 of this embodiment has the same structure as the structure of Embodiment 1.

The reaction device 10 is used for production of aldehyde in which: a gas supplied from the gas supplier 20 via the flow volume controller 21 is joined with alcohol as a raw material or a mixture containing alcohol as a raw material supplied from the raw material alcohol supplier 11 via the raw material supplying pump 12 to form a gas phase containing reaction fluid; the gas phase containing reaction fluid is supplied to the preheating section 13 and preheated in the preheating section 13; the preheated gas phase containing reaction fluid is supplied from the preheating section 13 to the reactor 14 to bring alcohol into reaction, thereby generating aldehyde and hydrogen in the reactor 14; the gas phase containing reaction fluid containing the produced aldehyde is supplied from the reactor 14 to the cooler 16, cooled and condensed; and the reaction fluid obtained from the cooler 16 is stored in the product reservoir 17.

<Method for Producing Aldehyde>

Next, a method for producing aldehyde using the reaction device 10 of Embodiment 2 is described.

As in Embodiment 1, the aldehyde production method of this embodiment is for producing a mixture of aldehyde and hydrogen from alcohol based on Formula 1 shown above.

According to the aldehyde production method of Embodiment 2, a reaction fluid, i.e., alcohol as a raw material or a mixture containing alcohol as a raw material is supplied from the raw material alcohol supplier 11 via the raw material supplying pump 12.

Alcohol as a raw material or a mixture containing alcohol as the raw material has the same structure as that described in Embodiment 1.

According to the aldehyde production method of Embodiment 2, a gas is supplied from the gas supplier 20 via the flow volume controller 21.

Examples of the gas include gases inert to the above-described chemical reaction, such as nitrogen, argon, helium, etc.

According to the aldehyde production method of Embodiment 2, alcohol or a mixture containing alcohol is joined with a gas to form a gas phase containing reaction fluid and the reaction fluid is supplied to the preheating section 13.

The effect of suppressing a side reaction and increasing aldehyde selectivity can be achieved and, for this reason, the gas phase containing reaction fluid is preferably formed so as to contain a low content of alcohol. Specifically, a molar fraction of alcohol is preferably 50 mol % or less, and more preferably 20 mol % or less.

Before the reaction fluid is supplied to the reactor 14, the phase state of the reaction fluid may be gas or may be in a mixing phase state of gas and liquid or gas and a supercritical fluid. After the reaction fluid is supplied to the reactor 14, the reaction fluid is preferably in a gas state. The phase state of the reaction fluid is controlled by adjusting the heating temperature of the reactor 14 by the heater 18 and setting the pressure of the reaction fluid by a pressure regulator (not shown) provided upstream of the product reservoir 17.

Process steps subsequent to preheating of the reaction fluid in the preheating section 13 are the same as those in Embodiment 1.

EXAMPLES

We carried out aldehyde production experiments on examples and comparative examples described below and calculated the reaction consumption rate of alcohol and the aldehyde selectivity. The reaction consumption rate of alcohol and the aldehyde selectivity were calculated as described below.

—Reaction Consumption Rate of Alcohol—

Sampled liquid collected after a reaction fluid stored from a reactor was sufficiently condensed was subjected to gas chromatography analysis to quantitatively measure the concentration of alcohol. The product by multiplication of the concentration and the quantity of the sampled liquid represents the quantity of unreacted alcohol. The value of 100% minus the percentage of the quantity of unreacted alcohol relative to the amount of the supplied alcohol as a raw material represents the reaction consumption rate.

—Aldehyde Selectivity—

Sampled liquid collected after a reaction fluid stored from a reactor was sufficiently condensed was subjected to gas chromatography analysis to quantitatively measure the concentration of each of aldehyde and ester. The value obtained by aldehyde/(aldehyde+ester)×100 (%) represents aldehyde selectivity.

Gas chromatography analysis used for obtaining the reaction consumption rate of alcohol and the aldehyde selectivity was conducted using a device called "6850 SeriesII" available from Agilent Technologies, Inc. equipped with a HP-ULTRA2 capillary column (12.0 m×200 μm×0.33 μm).

Example 1

The reaction device of Example 1 has the same structure as that shown in FIG. 4. Specifically, the raw material supplying pump is a microfeeder; the preheating section is made of SUS316 and has a circular tube flow path with an inside diameter of 1.0 mm and a length of 1 m; the reactor is made of SUS and has a linear tube reaction flow path with an inside diameter of 1.0 mm and a length of 3 m; the cooler is of air-cooling type, is made of SUS and has a circular tube flow path with an inside diameter of 1.0 mm and a length of 0.15 m; and the heater includes an oil bath capable of heating the preheating section and the reactor to and maintaining them at 220° C. by means of a heat transmitting by silicon oil. In the reaction flow path in the reactor, copper wires (reduced copper for elementary analysis, Lot. SDQ2757, manufactured by Wako Pure Chemical Industries, Ltd.) of 6.81 g, which have been sufficiently reduced in advance, each having a diameter of 600 μm and a length of 5 mm are disposed as a metal catalyst in series so as to extend substantially in parallel to the flow path of a fluid.

Using the reaction device of Example 1, 1-decanol (Kalcol 1098 (product name), Lot. 2161, manufactured by Kao Corporation) was supplied from the raw material alcohol supplier at 0.157 mL/h and nitrogen gas (having a purity of 99.999%<) was supplied from the gas supplier at 0.922 cc/min. Then, a reaction fluid of mixture of these materials was supplied to the preheating section while the reaction residence time τ of the reaction fluid in the reactor was controlled to be 13 seconds.

The reaction fluid in a gas-liquid mixing state obtained from the cooler was stored in the screw tube and then the liquid composition of the reaction fluid was analyzed.

As a result, the alcohol reaction consumption rate was 25.7%. The aldehyde selectivity was 98.7%.

Example 2

A reaction device having the same structure as the reaction device of Example 1 was prepared.

Using the reaction device of Example 2, 1-decanol (Kalcol 1098 (product name), Lot. 2161, manufactured by Kao Corporation) was supplied from the raw material alcohol supplier at 0.0509 mL/h and nitrogen gas (having a purity of 99.999%<) was supplied from the gas supplier at 0.300 cc/min. Then, a reaction fluid of mixture of these materials was supplied to the preheating section while the reaction residence time r of the reaction fluid in the reactor was controlled to be 39.9 seconds.

The reaction fluid in a gas-liquid mixing state obtained from the cooler was stored in the screw tube and then the liquid composition of the reaction fluid was analyzed.

As a result, the alcohol reaction consumption rate was 41.9%. The aldehyde selectivity was 91.9%.

Example 3

A reaction device having the same structure as the reaction device used in Example 1, except for the point that the reactor is made of SUS and has a linear tube reaction flow path with an inside diameter of 0.81 mm and a length of 3 m and the heater is an electric furnace capable of heating the preheating section and the reactor to and maintaining them at 220° C. by means of a radiation heat transmitting and the point that in the reaction flow path in the reactor, copper wires (reduced copper for elementary analysis, Lot. SDQ2757, manufactured by Wako Pure Chemical Industries, Ltd.) of 6.76 g, which have been sufficiently reduced in advance, each having a diameter of 600 μm and a length of 5 mm and being disposed as a metal catalyst in series so as to extend substantially in parallel to the flow path of a fluid.

Using the reaction device of Example 3, 1-decanol (Kalcol 1098 (product name), Lot. 2161, manufactured by Kao Corporation) was supplied from the raw material alcohol supplier at 0.157 mL/h and nitrogen gas (having a purity of 99.999%<) was supplied from the gas supplier at 0.922 cc/min. Then, a reaction fluid of mixture of these materials was supplied to the preheating section while the reaction residence time τ of the reaction fluid in the reactor was controlled to be 45.6 seconds.

The reaction fluid in a gas-liquid mixing state obtained from the cooler was stored in the screw tube and then the liquid composition of the reaction fluid was analyzed.

As a result, the alcohol reaction consumption rate was 25.8%. The aldehyde selectivity was 93.6%.

Comparative Example 1

A reaction device having the same structure as the reaction device used in Example 1, except for the point that the reactor is made of SUS and has a linear tube flow path with an inside diameter of 14.8 mm and a length of 5 cm and the point that in the reaction flow path in the reactor, copper particles (reduced copper for elementary analysis, having a particle size of 300 to 850 μm and 20 to 50 meshes, Lot. PKK3341, manufactured by Wako Pure Chemical Industries, Ltd.) of 21.21 g, which have been sufficiently reduced in advance are filled as a metal catalyst.

Using the reaction device of Comparative Example 1, 1-decanol (Kalcol 1098 (product name), Lot. 2154, manufactured by Kao Corporation) was supplied from the raw material alcohol supplier at 3.232 mL/h and nitrogen gas (having a purity of 99.999%<) was supplied from the gas supplier at 19.0 cc/min. Then, a reaction fluid of mixture of these materials was supplied to the preheating section while the reaction residence time τ of the reaction fluid in the reactor was controlled to be 2.4 seconds.

The reaction fluid in a gas-liquid mixing state obtained from the cooler was stored in the screw tube and then the liquid composition of the reaction fluid was analyzed.

As a result, the alcohol reaction consumption rate was 26.1%. The aldehyde selectivity was 82.9%.

CONCLUSION

Table 1 shows structures for reaction flow paths of reactors and the like in the reaction devices used in Examples 1 through 3 and Comparative Example 1 and evaluation results of examinations for the reaction devices.

TABLE 1

|  |  |  | Example 1 | Example 2 | Example 3 | Comparative Example 1 |
|---|---|---|---|---|---|---|
| Reactor | Inner diameter | mm | 1.0 | 1.0 | 0.81 | 14.8 |
|  | Length | m | 3.0 | 3.0 | 3.0 | 0.05 |
|  | Volume before filling catalyst | cm$^3$ | 2.36 | 2.36 | 1.55 | 8.60 |
| Catalyst | Form | — | Linear | Linear | Linear | Particles |
|  | Used amount | g | 6.81 | 6.81 | 6.76 | 21.21 |
|  | Surface area S | cm$^2$ | 51 | 51 | 51 | 4715 |
|  | ΣA2/ΣA1 | — | 0.028 | 0.028 | 0.028 | 0.25 |
| Reaction conditions | Reaction time | Hr | 480 | 870 | 480 | 490 |
|  | Temperature | °C. | 220 | 220 | 220 | 220 |
|  | Pressure | kPa | 101.3 | 101.3 | 101.3 | 101.3 |
|  | Reaction residence time τ | s | 13.0 | 39.9 | 45.6 | 2.4 |
| Results | Alcohol reaction consumption rate | mol % | 25.7 | 41.9 | 25.8 | 26.1 |
|  | Aldehyde selectivity | mol % | 98.7 | 91.9 | 93.6 | 82.9 |

By comparing Examples 1 through 3 and Comparative Example 1, it is understood that the aldehyde selectivity is high at the same alcohol reaction consumption rate in the reaction devices having a surface formed so that the catalyst provided in the reactor extends in the direction of flow of the reaction fluid.

The invention claimed is:

1. A reaction device for use in production of aldehyde from alcohol, the device comprising a reactor having a reaction field where a catalyst is provided inside and a reaction fluid flows,
wherein the catalyst has a surface extending in a direction of flow of the reaction fluid and contains Cu, and
wherein ΣA2/ΣA1 obtained by dividing a total sum ΣA2 of a projected area A2 of a unit of catalyst on a plane perpendicular to the direction of flow of the reaction fluid by a total sum ΣA1 of a surface area A1 of the unit of catalyst is 0 to 0.1.

2. The reaction device of claim 1, wherein the catalyst continuously extends in the direction of flow of the reaction fluid.

3. The reaction device of claim 1, wherein the catalyst has an elongated structure.

4. The reaction device of claim 1, wherein the catalyst constitutes the inner wall of the reactor.

5. The reaction device of claim 1, wherein the catalyst is composed of a simple substance of Cu.

6. The reaction device of claim 1, wherein the reaction fluid to be supplied to the reactor is a gas phase containing reaction fluid resulting from dilution of alcohol as a raw material or a mixture containing alcohol as a raw material with an inert gas or a gas phase containing reaction fluid resulting from putting alcohol as a raw material or a mixture containing alcohol as a raw material under reduced pressure.

7. A method for producing aldehyde from alcohol, wherein a reaction fluid containing alcohol is made to flow and react in a reaction field where a catalyst having a surface extending in a direction of flow of the reaction fluid and contains Cu is provided, thereby producing aldehyde,
wherein a ratio ΣA2/ΣA1, obtained by dividing a total sum ΣA2 of a projected area A2 of a unit of the catalyst on a plane perpendicular to the direction of the flow of the reaction fluid by a total sum ΣA1 of a surface area A1 of the unit of catalyst, is 0 to 0.1.

8. The method of claim 7, wherein the reaction fluid is a gas phase containing reaction fluid resulting from dilution of alcohol as a raw material or a mixture containing alcohol as a raw material with an inert gas or a gas phase containing reaction fluid resulting from putting alcohol as a raw material or a mixture containing alcohol as a raw material under reduced pressure.

9. The reaction device of claim 1, wherein the catalyst is in the form of wires and the wires are oriented in a lengthwise direction extending in the direction of flow of the reaction fluid.

10. An alcohol dehydrogenation reaction device, comprising:
a reactor and a catalyst;
wherein the catalyst is present in a reaction field of the reactor and the reaction field conducts a reaction fluid flow,
wherein the catalyst has a surface extending in a direction of flow of the reaction fluid;
wherein the catalyst contains copper, and
wherein ΣA2/ΣA1, obtained by dividing a total sum ΣA2 of a projected area A2 of a unit of catalyst on a plane perpendicular to the direction of the reaction fluid flow by a total sum ΣA1 of a surface area A1 of the unit of catalyst, is 0 to 0.1.

11. The reaction device of claim 10, wherein the catalyst is present in the entire length of the reaction field.

12. The reaction device of claim 10, wherein the catalyst consists of copper.

13. The reaction device of claim 10, further comprising a heater and a preheater, wherein the preheater is upstream of the reactor and the heater heats both the preheater and the reactor.

14. A method for dehydrogenating an alcohol to form an aldehyde, comprising:
heating the alcohol; and
contacting the heated alcohol with a catalyst;
wherein the catalyst is present in the reaction field of the reactor,
wherein the catalyst has a surface extending in a direction of flow of the reaction fluid;
wherein the catalyst contains copper; and
wherein ΣA2/ΣA1, obtained by dividing a total sum ΣA2 of a projected area A2 of a unit of catalyst on a plane perpendicular to the direction of the flow of the reaction fluid by a total sum $\Sigma A1$ of a surface area A1 of the unit of catalyst, is 0 to 0.1.

15. The method of claim 14, further comprising:

adding a gas to the alcohol before the contacting;

wherein the reaction fluid is in the form of a gas during the contacting.

16. The method of claim 14, wherein the reaction fluid is in the gas phase and comprises an alcohol raw material.

17. The method of claim 14, wherein the reaction fluid is in the gas phase and is a mixture containing an alcohol as a raw material and an inert gas.

18. The method of claim 14, wherein the contacting is carried out by flowing a gaseous mixture of the alcohol and an inert gas in the reaction field of the reactor.

* * * * *